Dec. 25, 1951 E. S. BOERNER Plant Pat. 1,056
ROSE PLANT
Filed July 18, 1950
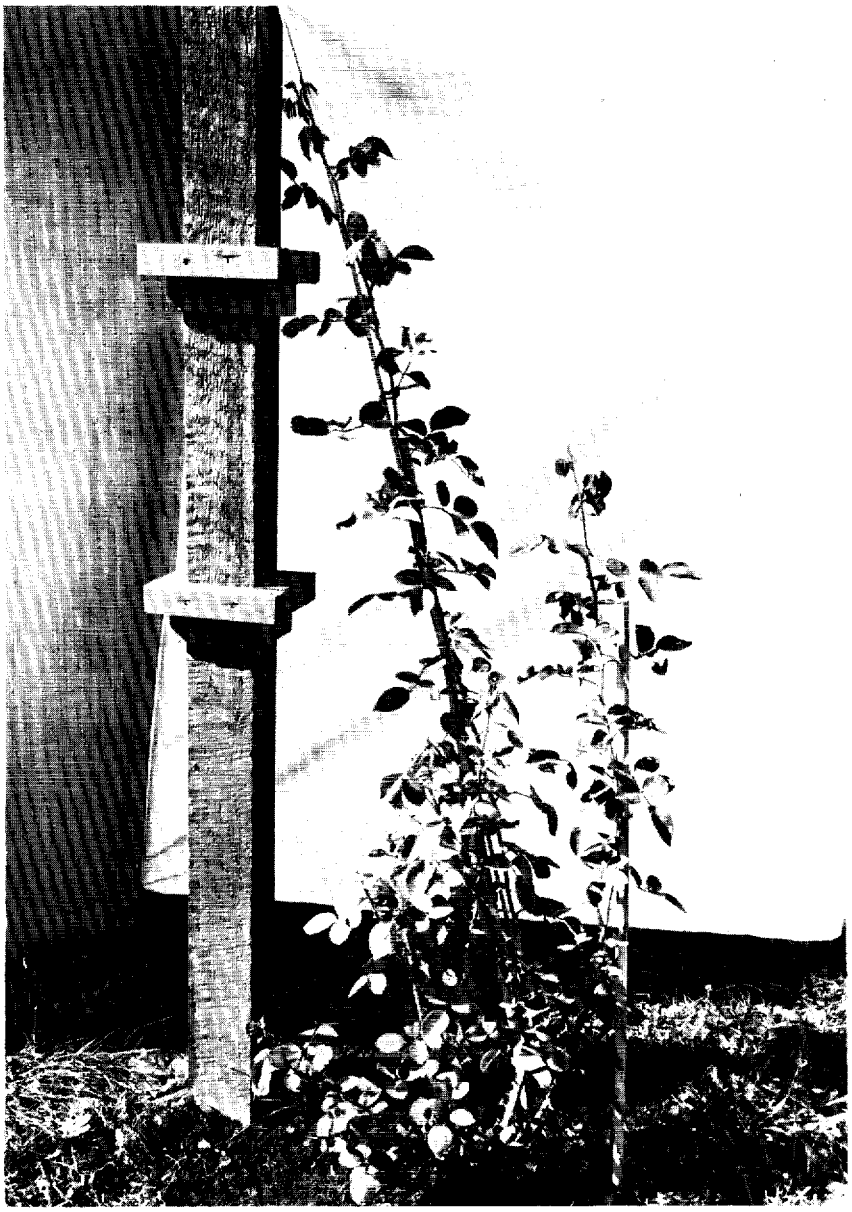
Inventor.
E. S. Boerner
By: Robert Cobb
Attorneys.

Patented Dec. 25, 1951

Plant Pat. 1,056

UNITED STATES PATENT OFFICE 1,056

ROSE PLANT

Eugene S. Boerner, Newark, N. Y., assignor to Jackson & Perkins Company, Newark, N. Y., a corporation of New York Application July 18, 1950, Serial No. 174,551

1 Claim. (Cl. 47—61)

The present invention relates to a new and distinct variety of rose plant, originating as a cultivated sport of the variety "New Yorker" (Plant Patent No. 823), and distinguished therefrom by its climbing habit of growth.

The parent variety is a bush rose of the hybrid tea class and is notable for its vigor and hardy growth, by the characteristic markings of Oxblood Red color on the under side of the old foliage, by its extremely free blooming habit, by the velvety, vibrant deep red color of its flowers, by the high centered form of the flowers and the perfect reflex habit of the petals thereof, and by the characteristic strong veining on the inside of the petals.

The new variety herein was discovered among several hundred plants of ordinary bush form, growing in the greenhouse under my control and supervision and owned by my employer-assignee, but this particular plant threw long canes which attracted my attention thereto. The flowers, buds and foliage of the new variety are the same as those of the parent, but the new variety is dominantly distinguished from its parent by the long, climbing basal shoots which attain a height of from six to eight feet, and which bear flowers on short axillary flowering branches as soon as the climbing growth has ceased.

Asexual reproduction of the new variety by budding at Newark, New York, and at Pleasanton, California, shows that the foregoing characteristics come true to form and are established and transmitted through succeeding propagations.

The accompanying drawing shows a specimen plant and illustrates its characteristic climbing habit of growth.

The following is a detailed description of the new variety, with color terminology in accordance with Ridgway's Color Standards and Nomenclature:

Parentage: Sport of "New Yorker."
Classification: Botanic and commercial — climber.

*Flower*

(Observations made in the greenhouse at Newark, New York in the early morning of June 25, 1949.)

Blooming habit: Recurrent—continuous.

Bud:

*Size.*—Large.

*Form.*—Ovoid. Is not affected by wet or hot weather.

*Color.*—When sepals first divide—Oxblood Red, Plate 1. When petals begin to unfurl—Carmine, Plate 1. When half blown—inside of petals: Carmine, Plate 1; reverse of petals: Between Rose Red, Plate 12, and Pomegranate Purple, Plate 12.

Sepals.—Branched. Curl back when petals begin to unfurl. Color—inside—Kildare Green, Plate 31; outside—Rainette Green, Plate 31.

*Calyx.* — Shape — pear. Size — small. Aspect—smooth. Odor when rubbed—none. Color—Light Bice Green, Plate 17.

*Peduncle.* — Length — medium. Aspect — rough. Color—Light Hellebore Green, Plate 17. Strength—erect; slender.

*Opening.*—Bud opens up well. Is not affected by adverse weather conditions.

Bloom:

*Size.*—Large. Average size when fully expanded—4½ inches to 5 inches.

*Borne.*—Singly and several together.

*Stems.*—Long; strong.

*Form.*—When first open—high center. Permanence—retains its form to near the end; becomes open-centered and flattens somewhat when fully expanded.

*Petalage.*—Double (full but open center). Number of petals under normal conditions, 35.

*Color.*—Center of flower—Nopal Red, Plate 1. Outer petals—Carmine, Plate 1, overlaid with Rose Red, Plate 12. Base of petals (aiglet)—Sulphur Yellow, Plate 5. Inside of petals—Carmine, Plate 1, overlaid with Rose Red, Plate 12. Reverse of petals—Pomegranate Purple, Plate 12, overlaid with Rose Red, Plate 12. General tonality from a distance—Carmine, Plate 1, overlaid with Rose Red, Plate 12.

*Discoloration.*—General tonality at end of first day—Carmine, Plate 1, overlaid with Rose Red, Plate 12. Second day—Carmine, Plate 1, overlaid with Rose Red, Plate 12. Third day—Nopal Red, Plate 1, overlaid with Rose Red, Plate 12.

Petals:

*Texture.*—Thick. Is not affected by wet or hot weather.

*Appearance.* — Inside — velvety. Outside—satiny.

*Form.*—Oval pointed.

*Arrangement.* — Imbricated (regularly arranged shingle-like). Petaloids in center—few; large.

*Persistence.*—Drop off cleanly.

*Fragrance.*—Moderate. Nature—fruity (Russet apple).

*Lasting quality.*—On the plant and as cut flower—long.

Genital organs:

*Stamens, anthers.* — Medium size; many. Color—Buff Yellow, Plate 4. Arrangement—regular around styles.

*Stamens, filaments (threads).* — Medium length. Color—Spectrum Red, Plate 1.

*Pollen.*—Color—Maize Yellow, Plate 4.

*Styles.* — Bunched; uneven length; short; heavy.

*Stigmas.*—Color—Maize Yellow, Plate 4.

*Ovaries.*—All enclosed in calyx.

*Plant*

Form: Climber.

Growth: Vigorous; 6 foot to 8 foot shoots.

Foliage: 5 to 7 leaflets.

*Size.*—Large.

*Quantity.*—Normal.

*Color.*—New foliage—upper side—Victoria Lake, Plate 1; under side—Oxblood Red, Plate 1. Old foliage.—upper side—Dark Cress Green, Plate 31; under side—Hellebore Green, Plate 17.

*Shape.*—Oval pointed.

*Texture.* — Upper side — leathery. Under side—smooth. Ribs and veins—ordinary.

*Edge.*—Serrated (saw toothed).

*Serrations.*—Single; small.

*Leaf stem.*—Color—Kronberg's Green, Plate 31. Under side—prickles.

*Stipules.*—Long; bearded.

*Disease resistance.*—Resistant.

Wood:

*New wood.*—Color—Auburn, Plate 2. Bark—smooth.

*Old wood.*—Color—Cedar Green, Plate 6. Bark—smooth.

Thorns:

*Thorns.*—Quantity—on main stalks from base—many. On laterals from stalk—ordinary. Form—broad base; medium length; hooked downward. Color when young—Nopal Red, Plate 1. Position—irregular.

*Prickles.*—Quantity—on main stalks—none; on laterals—few. Color—Lettuce Green, Plate 5.

*Short needles.*—None.

I claim:

A new and distinct variety of rose plant, characterized as to novelty by its similarity to its parent "New Yorker" (Pl. Pat. No. 823) in respect to its buds, flowers and foliage, but distinguished therefrom by its vigorous and upright climbing basal shoots which bear flowers on short axillary flowering branches as soon as the climbing growth has ceased, substantially as shown and described.

EUGENE S. BOERNER.

No references cited.